United States Patent [19]

Haber et al.

[11] Patent Number: 5,257,978
[45] Date of Patent: Nov. 2, 1993

[54] IV SAFETY MODULE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 914,173

[22] Filed: Jul. 14, 1992

[51] Int. Cl.⁵ .................. A61M 5/00; A61M 1/00
[52] U.S. Cl. ...................... 604/250; 604/153; 417/480; 251/9
[58] Field of Search ............ 604/250, 153, 213; 128/DIG. 13; 251/9, 10; 417/474, 480

[56] References Cited

U.S. PATENT DOCUMENTS

| | | | |
|---|---|---|---|
| 4,155,362 | 5/1979 | Jess | 604/153 |
| 4,586,691 | 5/1986 | Kozlow | 604/250 |
| 4,689,043 | 8/1987 | Bisha | 604/250 |
| 5,017,192 | 5/1991 | Dodge et al. | 604/250 |
| 5,055,001 | 10/1991 | Natwick et al. | 417/479 |
| 5,116,203 | 5/1992 | Natwick et al. | 604/153 |

*Primary Examiner*—John G. Weiss
*Attorney, Agent, or Firm*—Townsend & Townsend Khourie & Crew

[57] ABSTRACT

An IV safety module (2) is used with a peristaltic type IV pump (5) to prevent the unrestricted flow of IV fluid through an IV line (4) when the door (80) of the IV pump is open. A locking trigger (42) is pivotally mounted to the body. A spring (10) is mounted to the body and has a section (18) which compresses and collapses the IV tube closed, thus substantially halting and IV fluid flowing therethrough, as the spring biases the trigger to the tube clamped position. The safety module is mounted adjacent the pump and is configured so that closing the door of the pump depresses the trigger to open the IV tube.

9 Claims, 6 Drawing Sheets

IV SAFETY MODULE

BACKGROUND OF THE INVENTION

Intravascular administration of fluids is ubiquitous in modern medical practice. These fluids encompass a wide variety, but they are generally water-based. Examples include saline solutions such as "normal saline" or sterile water mixed with sodium chloride to a final concentration of about 0.9%. Other concentrations of saline solution, such as one-half or one-quarter the amount found in normal saline, are also widely used. Further examples of commonly employed intravascular fluids include Ringer's solution, lactated Ringer's solution, and water-based solutions which have other additives. These additives are too numerous to name, but include substances such as potassium chloride, potassium phosphate, glucose or dextrose, magnesium, phosphorus, calcium and many other compounds and elements.

The indications for administering fluids are myriad and are well known in the art. A few of the many indications include dehydration, inability to take fluids by the oral route, and a need for medications which are most efficacious if administered intravascularly. Intravenous fluid administration is more widely practiced than intra-arterial administration, but both are examples of intravascular access to a patient.

Intravenous drug therapy is well known in medical practice. Typically water soluble drugs are used. A few examples of some of the many intravenous medications in use include diuretics such as lasix, cardiac medications such as lidocaine, antibiotics such penicillin and aminoglycosides, hormones such as oxytocin and cortisone, analgesics such morphine sulfate, and chemotherapeutic agents such adriamycin and cis-platinum which are used in cancer therapy. In addition to these drugs and the previously mentioned fluids, intravenous therapy is also widely practiced for transfusions of blood and various blood components such as washed packed red cells and platelets.

Methods of instituting intravenous therapy, such as intravenous fluid or drug therapy, are well known in the art and will only be briefly summarized here. A fluid source, usually a soft-sided plastic bag, contains a sterile fluid suitable for use in humans. The bag includes an access port to which a line or tubing is connected by means which frequently include a cannula. This tubing is in fluid communication with the patient's circulatory system through means which usually include a hollow needle cannula. The needle end is placed into the patient's blood vessel and the opposite end connects to the tubing.

Although intravenous methods are most frequently used for intravascular therapy, intra-arterial therapy is also known and practiced. Because an arterial typically has higher native internal pressure than a vein, there are special problems involved in administering fluids or drugs intra-arterially. Use of an intra-arterial access device typically requires maintenance of higher pressure to deliver fluids as compared to an intravenous method.

When administering intravascular fluids or other substances, it is frequently convenient to include a pumping mechanism along the line or tubing. This pump, which is often a peristaltic-type pump, assists in delivering a precise volume at a specified rate. If a pump is not used, some other flow monitoring means are used. For instance, the clinician or assistant may rely on gravity to create a pressure differential between the bag and the patient's vascular access to achieve flow. This usually consists of placing the bag or fluid source higher than the level of the entry point of the fluid into the patient. A rotatable knob at the exit portion of the bag is manipulated to control egress of the fluid. The pump method can be more accurate and reliable in delivering the desired flow.

The pump generally involves a gear mechanism including rollers which accept the intravenous tubing. Pressure of the rotating rollers squeezes or milks the tubing to allow flow of fluid from the fluid source to the patient. Usually the tubing is curved over the gear mechanism which is covered by a door. The typical arrangement is that when the door is opened the tubing is not compressed at the point where the tubing enters the pump and thus free flow of the fluid is temporary permitted. Unfortunately it is frequently necessary to open the door to adjust the tubing or to solve some problem which has caused the machine to emit a warning beep or light. During this time, that is, when the door is open, there exists a risk of inappropriate fluid flow from the fluid source to the patient. Additional compromise can occur if the door is inadvertently left open or is not completely closed. This inadvertence can lead to inaccurate dosing of the fluid or medication contained in the fluid. Because the fluid flow is less restricted when the door is open than when the door is shut, inadvertence in leaving the pump door open would lead to overdosage of the patient with the fluid or medication.

SUMMARY OF THE INVENTION

The present invention is directed to an IV safety module for use with an IV assembly of the type including an IV bag or other fluid source, an IV line and, preferably, a peristaltic type IV pump along the IV line coupling the fluid source to the patient. The present invention provides a safety feature for pumps of the type described above, and use of the invention can enhance accurate dosing of a patient receiving intravenous fluids of medications. Additionally, the principles of the invention can be applied to pumps for use with intra-arterial fluid lines.

The IV pump is of a type having a door which opens providing access to the section of the IV line which is engaged by rollers to pump the IV fluid along the IV line. The module includes a body mountable to the IV line adjacent the IV pump. A moveable locking trigger is mounted to the body for movement between tube clamped closed and tube open positions. A spring is secured to the body and biases the locking trigger toward the tube clamped closed position. In this position a section of the spring collapses a portion of the IV tube thus halting flow of IV fluid through the IV tube.

One of the primary advantages of the invention is that it can be used with an existing IV pump, such as the Model 599B made by IVAC of San Diego, Calif., to insure additional safety by preventing unrestricted flow of the IV fluid to the patient.

Another advantage of the invention is that the normally closed aspect of the safety module can be overridden to allow for operation without the IV pump. However, with the construction of the safety module, and the IV pump in place, the pump door cannot be closed until the safety module is no longer disabled, typically by sliding the locking trigger back to its normal, enabled position.

The spring serves several functions. First, it acts as a clamping bar which pushes against and collapses the IV tubing. Second, it acts as an actuating arm which pushes upwardly on the trigger. Third, it acts as the source for the spring biasing force for these functions.

Other features and advantages of the invention will appear from the following description which the preferred embodiment has been set forth in detail in conjunction with the accompanying drawings.

DESCRIPTION OF THE PREFERRED EMBODIMENT

FIGS. 1 and 2A–2C show an IV safety module 2 in conjunction with an IV line 4 through which an IV fluid is directed from an IV source (not shown) to a patient (not shown). Safety module 2 is used in conjunction with an IV peristaltic pump 5, such as the Volumetric Pump made by IVAC of San Diego, Calif. as Model 599B. The portions of the peristaltic pump pertinent to the construction and use of safety module 2 will be discussed below in conjunction with FIGS. 3A and 3B.

Figure 1:
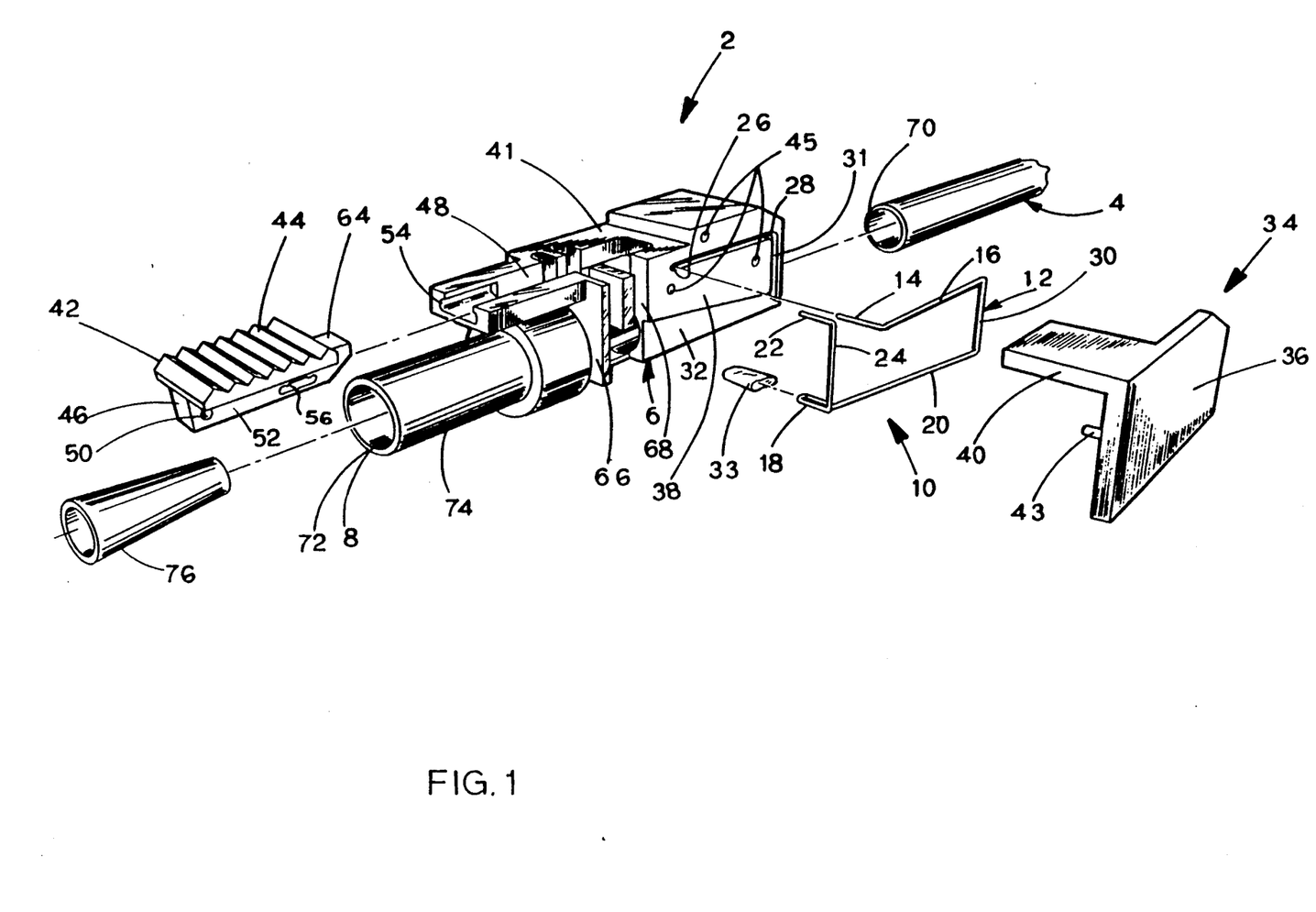
FIG. 1 is an exploded perspective view of an IV safety module made according to the invention.

Module 2 includes a body 6 having a central bore 8 through which IV line 4 passes. A clamp spring 10 is mounted to body 6 and includes a U-shaped spring portion 12 having a first tip 14 extending from an upper arm 16 of portion 12 and a tube clamp section 18 extending from a lower arm 20 of portion 12. Spring 10 also includes a second tip 22 connected to section 18 by a connecting arm 24. Tip 14 passes into a hole 26 in body 6 while upper arm 16 is housed in a slot 28. A vertical portion 30 of U-shaped portion 12 is housed within a slot 31 formed in body 6. Lower arm 20 is positioned along a recessed surface 32. Spring 10 is held in position by use of a retaining plate 34 which includes a face portion 36, secured to the face 38 of body 6, and an overlying portion 40, which lies within a recessed portion 41 of body 6. Plate 36 includes three cylindrical pegs 43, each about 0.12 inch (3 mm) long positioned to engage complementary holes 45 formed in face 38 of body 6.

Figure 2A:
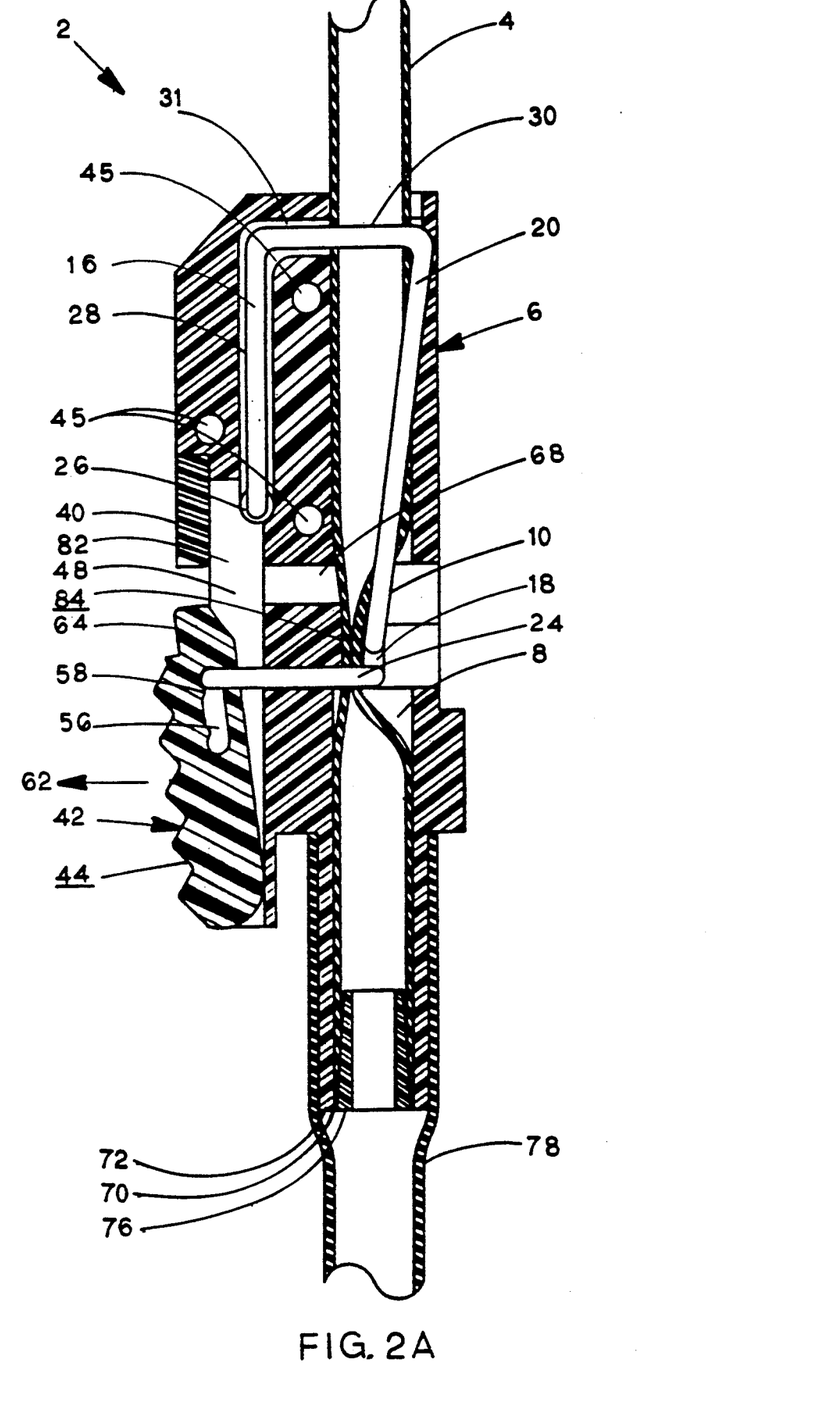
FIG. 2A is a cross-sectional assembled view of the module of FIG. 1 with the locking trigger in the enabled, tube clamped position.
Figure 2B:
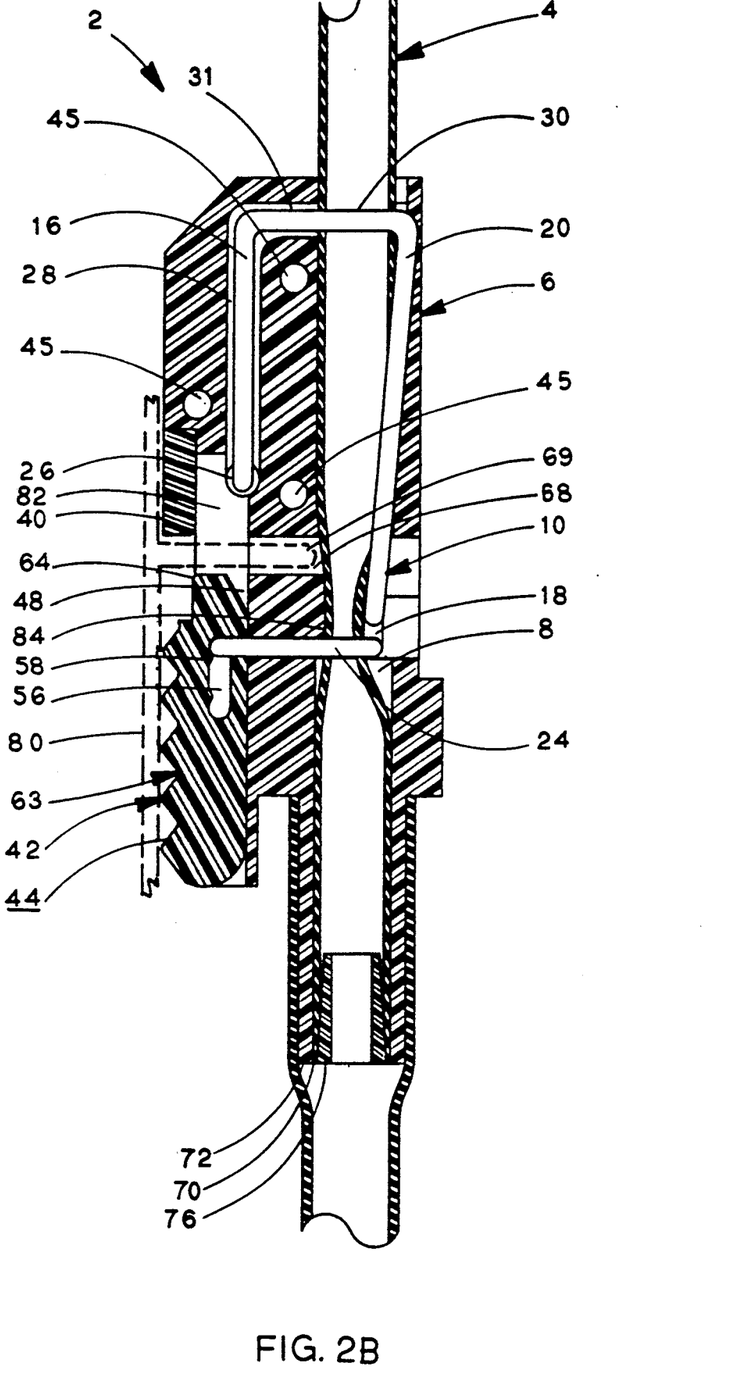
FIG. 2B shows the module of FIG. 2A with the locking trigger in the enabled, tube released position and with portions of the door of the IV pump shown in dashed lines.

A locking trigger 42 is movably mounted to body 6 for pivotable movement between an enabled, tube clamped closed position of FIG. 2A and enabled, tube released position of FIG. 2B by the application of a force in the direction of arrow 63. This force can be applied by door 80 of IV pump 5 as suggested in FIG. 2B. Trigger 42 includes a serrated upper surface 44 to provide good frictional engagement for the user. The lower portion of trigger 42 includes a downwardly extending rib 46 which rides within a slot 48 formed along body 6. A pair of outwardly extending, rounded protrusions 50 extend laterally from the sides 52 of rib 46 and engage two semi-cylindrical cutouts 54 formed in slot 48. Thus, protrusions 50 within cutouts 54 allow trigger 42 to both slide axially within slot 48 and also pivot about protrusions 50.

A slot 56 is formed through rib 46 and is sized to accept second tip 22 of clamp spring 10. As shown in FIGS. 2A and 2B, second tip 22 is held within one end of slot 56 by a first detent 58; however, when trigger 42 is in the enabled tube released position of FIG. 2B (and assuming rib 69 of door 8, discussed below, has been removed from region 82 of slot 68), the user can move trigger 42 to the disabled, tube released position of FIG. 2C by moving, that is sliding, the trigger in the direction of arrow 60 of FIG. 2C so that second tip 22 moves to the other end of slot 56. This prevents pivotable movement of trigger 42 from the enabled, tube released position of FIG. 2B in the direction of arrow 62 to the enabled, tube clamped closed position of FIG. 2A by engagement of the tip 64 of locking trigger 42 beneath overlying portion 40 of retaining plate 34.

Body 6 includes a first, generally vertical slot 66 formed part way through the body and sized to receive tube clamp section 18, connecting arm 24 and second tip 22. Body 6 also includes a second, generally vertical slot 68 formed part way through body 6 positioned parallel to slot 66. Slot 68 is sized for receipt of a rib 69 on pump 5 as discussed below with reference to FIGS. 3A and 3B.

Figure 2C:
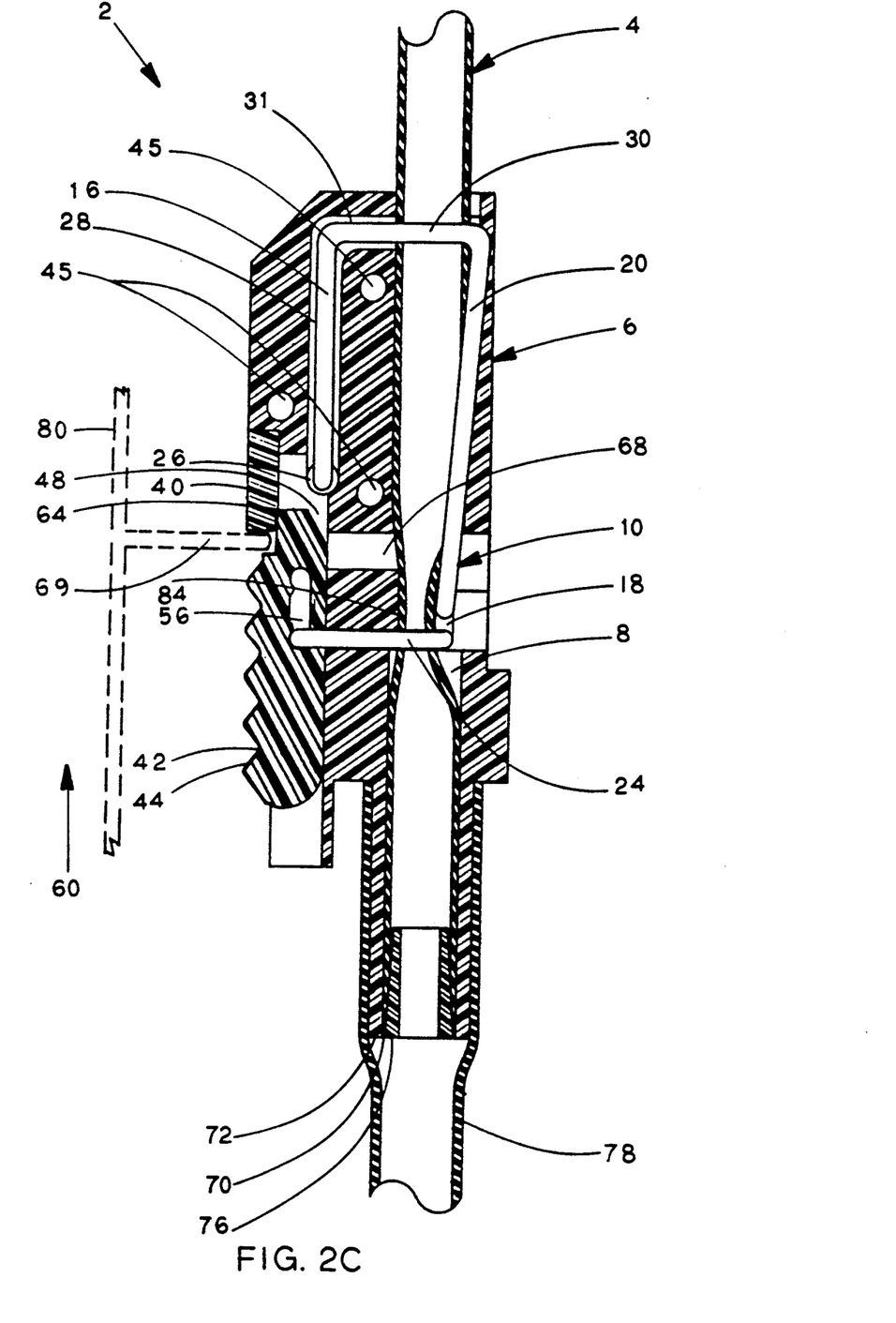
FIG. 2C shows the safety module of FIG. 2B with the locking trigger in the disabled, tube released position and with portions of the door of the IV pump shown in dashed lines.

IV line 4 passes through central bore 8 with the outer end 70 extending past the end 72 of tubular portion 74 of body 6. A hollow, tapered seal cone 76 is inserted into the interior of IV line 4 at end 70 and the IV line is drawn back into central bore 8 thus wedging line 4 within bore 8. Silicone pump tubing 78 is mounted over tubular portion 74 as shown in FIGS. 2A–2C.

Figure 3A:
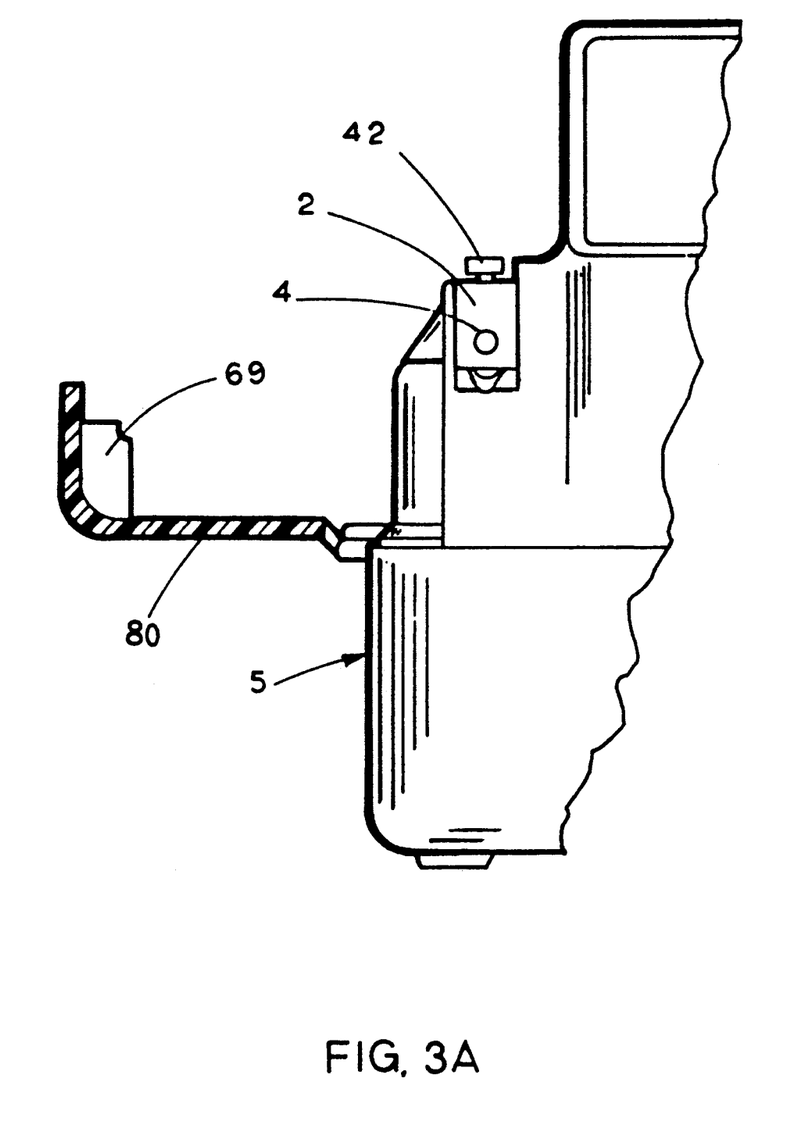
FIG. 3A is a simplified top view showing the module of FIG. 2A mounted within a peristaltic pump with the pump door open.
Figure 3B:
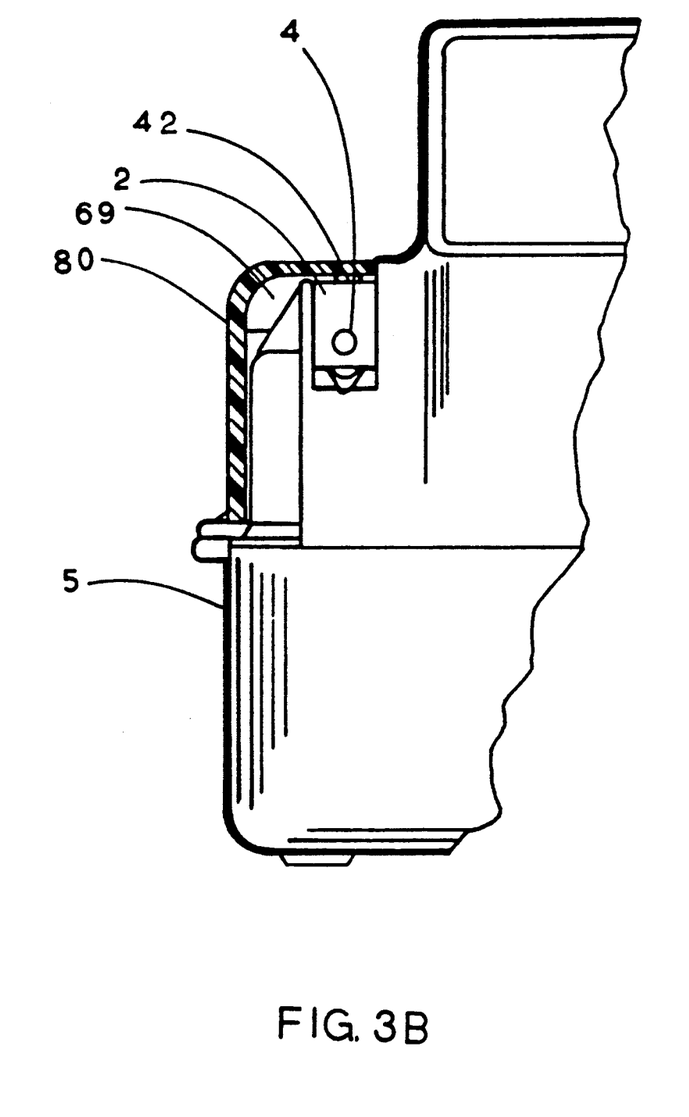
FIG. 3B shows the module of FIG. 3A with the door closed and the trigger in the position of FIG. 2B.

FIGS. 3A and 3B illustrate top views of pump 5 with safety module 2 mounted therein and door 80 in the open and closed positions. Although not clear from the simplified fragmentary view of FIGS. 3A and 3B, rib 69 of pump 5, used to keep IV line from pulling out of the pump, passes into slot 68 when door 80 is closed. A portion of rib 69 also enters a region 82 adjacent tip 64 of trigger 42. This is shown in FIG. 2B. Therefore, when safety module 2 is mounted within pump 5, trigger 42 is prevented from moving from the enabled, tube released position of FIG. 2B to the disabled, tube released position of FIG. 2C. If trigger 42 is in the disabled, tube released position of FIG. 2C, door 80 will not close all the way. See FIG. 2C. Pump 5 is constructed so that the pump will operate only when door is completely closed.

In use, outer end 70 of tube 4 is inserted through central bore 8 past end 72 of tubular portion 74. Seal cone 76 is inserted into outer end 70 and the outer end is pulled back into central bore 8 to wedge, and thus secure, outer end 70 within central bore 8. Pump tubing 78 is then slipped over tubular portion 74 and the assembly is mounted within pump 5 as shown in FIG. 3A. At this point, trigger 42 is in the enabled, tube clamped closed position of FIGS. 2A and 3A. Closing door 80 presses downwardly on trigger 42 thus opening IV line 4 by moving the trigger to the enabled, tube released position of FIGS. 2B and 3B.

Safety module 2 can also be used without pump 5. Removing the assembly of FIG. 2A from the pump 5 causes the tubing to be clamped shut. To permit fluid flow through IV line 4, trigger 42 is depressed to the position of FIG. 2B; to maintain trigger 42 in the depressed condition, trigger 42 is slid in the direction of arrow 60 to the disabled, tube released position of FIG. 2C.

Central bore 8 provides a generally cylindrical path over its entire length. However, a portion of central bore 8 above tubular clamp section 18 of clamp spring 10 is depressed somewhat to provide a flat surface 84, corresponding to the straight line section of tubular clamp section 18, directly above the tubular clamp section. This can be seen in FIG. 2A by the inward deflection of the wall of IV line 4 as line 4 passes through body 6 adjacent tubular clamp section 18. Doing so helps ensure good sealing of IV line 4. To help prevent wear on line 4, a resilient tube 33, shown only in FIG. 1, can be mounted over section 18 of spring 10.

Clamp spring 10 is shown sized to partially compress IV line 4 when trigger 42 is in the tube released positions of FIGS. 2B and 2C. Clamp spring 10 could be sized to leave IV line 4 undeflected in this position as well.

Other modifications and variations can be made to the disclosed embodiment without departing from the subject of the invention as defined in the following claims. For example, trigger 42 could be a linear acting, rather than a pivotally acting element.

What is claimed is:

1. An IV safety module, for use with an IV assembly of the type including an IV fluid source, an IV line coupled to the IV fluid source and an IV pump along the IV line which pumps a selected flow of IV fluid through the IV line to the patient, the IV pump being of the type which forces the IV fluid along a pump section of the IV line mountable within the IV pump, the IV pump having a door movable between an open position, which exposes the pump section of the IV line, and a closed position, which secures the pump section of the IV line within the pump, the safety module comprising:
a body mountable to the IV line; and
safety means for automatically clamping the IV line closed, to substantially prevent fluid flow therethrough, when the pump door is open, and for automatically unclamping the IV line, to permit substantially unhindered fluid flow therethrough, when the pump door is closed, the safety means including a locking trigger movably mounted to the body for movement between a tube clamped closed position, in which at least a part of the locking trigger is spaced apart from the body, and a tube released position, in which the at least part of the locking trigger is adjacent the body.

2. The IV safety module of claim 1 wherein the locking trigger is pivotally mounted to the body.

3. The IV safety module of claim 1 wherein the safety means includes a spring, mounted to the body and connected to the locking trigger, which biases the locking trigger from the tube released position to the tube clamped closed position.

4. An IV safety module, for use with an IV assembly of the type including an IV fluid source, an IV line coupled to the IV fluid source and an IV pump along the IV line which pumps a selected flow of IV fluid through the IV line to the patient, the IV pump being of the type which forces the IV fluid along a pump section of the IV line mountable within the IV pump, the IV pump having a door movable between an open position, which exposes the pump section of the IV line, and a closed position, which secures the pump section of the IV line within the pump, the door including a rib element which engages the pump section of the IV line when in the closed position, the safety module comprising:
a body mountable to the IV line;
safety means for automatically clamping the IV line closed, to substantially prevent fluid flow therethrough, when the pump door is open, and for automatically unclamping the IV line, to permit substantially unhindered fluid flow therethrough, when the pump door is closed;
the safety means including a locking trigger pivotally mounted to the body for movement between tube clamped closed and tube released positions;
means for disabling the safety means thereby keeping the trigger in the unclamped position so the IV line remains unclamped and substantially open, the disabling means including means for sliding the trigger between enabled and disabled positions; and
the rib element including means for preventing the door from moving to the closed position when the trigger is in the disabled position.

5. An IV safety module, for use with an IV assembly of the type including an IV fluid source, an IV line coupled to the IV fluid source and an IV pump along the IV line which pumps a selected flow of IV fluid through the IV line to the patient, the IV pump being of the type which forces the IV fluid along a pump section of the IV line mountable within the IV pump, the IV pump having a door movable between an open position, which exposes the pump section of the IV line, and a closed position, which secures the pump section of the IV line within the pump, the safety module comprising:
a body mountable to the IV line; and
safety means for automatically clamping the IV line closed, to substantially prevent fluid flow therethrough, when the pump door is open, and for automatically unclamping the IV line, to permit substantially unhindered fluid flow therethrough, when the pump door is closed, the safety means including a spring, mounted to the body and connected to the locking trigger, which biases the locking trigger from the tube released position to the tube clamped closed position, the spring having an IV line engaging portion which engages and collapses the IV line when the trigger is in the tube clamped closed position.

6. The IV safety module of claim 5 wherein the body includes an open region along which the IV line passes, the open region having a surface generally conforming to the shape of the IV line engaging portion to aid collapse of the IV line by the spring.

7. An IV safety module, for use with an IV assembly of the type including an IV fluid source, an IV line coupled to the IV fluid source and an IV pump along the IV line which pumps a selected flow of IV fluid through the IV line to the patient, the IV pump being of the type which forces the IV fluid along a pump section of the IV line mountable within the IV pump, the IV pump having a door movable between an open position, which exposes the pump section of the IV line, and a closed position, which secures the pump section of the IV line within the pump, the safety module comprising:

a body mountable to the IV line;

safety means for automatically clamping the IV line closed, to substantially prevent fluid flow therethrough, when the pump door is open, and for automatically unclamping the IV line, to permit substantially unhindered fluid flow therethrough, when the pump door is closed, the safety means including a spring, mounted to the body and connected to the locking trigger, which biases the locking trigger from the tube released position to the tube clamped closed position; and means for disabling the safety means thereby keeping the trigger in the unclamped position so the IV line remains unclamped and substantially open.

8. The IV safety module of claim 7 wherein the trigger is pivotally mounted to the body for movement between the tube clamped closed and tube unclamped positions.

9. The IV safety module of claim 8 wherein the disabling means includes means for sliding the trigger between enabled and disabled positions.

* * * * *